United States Patent
Hayakawa et al.

(10) Patent No.: US 11,691,861 B2
(45) Date of Patent: Jul. 4, 2023

(54) METHOD OF CLEANING AND STERILIZING DRINK FILLING APPARATUS

(71) Applicant: Dai Nippon Printing Co., Ltd., Tokyo (JP)

(72) Inventors: Atsushi Hayakawa, Tokyo (JP); Seiji Kuwano, Tokyo (JP)

(73) Assignee: DAI NIPPON PRINTING CO., LTD., Tokyo (JP)

( * ) Notice: Subject to any disclaimer, the term of this patent is extended or adjusted under 35 U.S.C. 154(b) by 492 days.

(21) Appl. No.: 16/648,012

(22) PCT Filed: Oct. 3, 2018

(86) PCT No.: PCT/JP2018/036975
§ 371 (c)(1),
(2) Date: Mar. 17, 2020

(87) PCT Pub. No.: WO2019/069967
PCT Pub. Date: Apr. 11, 2019

(65) Prior Publication Data
US 2020/0277178 A1    Sep. 3, 2020

(30) Foreign Application Priority Data
Oct. 4, 2017   (JP) ................................ 2017-194243

(51) Int. Cl.
*B67C 3/00*     (2006.01)
*A61L 2/07*     (2006.01)

(52) U.S. Cl.
CPC ............... *B67C 3/001* (2013.01); *A61L 2/07* (2013.01); *A61L 2202/17* (2013.01)

(58) Field of Classification Search
CPC .................................................... B67C 3/001
See application file for complete search history.

(56) References Cited

U.S. PATENT DOCUMENTS

2014/0286822 A1* 9/2014 Hayakawa ................. A23L 2/46
422/1
2015/0298178 A1* 10/2015 Hayakawa ............ B67C 7/0073
134/22.1
(Continued)

FOREIGN PATENT DOCUMENTS

JP    2007-022600 A    2/2007
JP    2007-215893 A    8/2007
(Continued)

OTHER PUBLICATIONS

Japanese Office Action (Application No. 2019-205780) dated Nov. 4, 2020 (with English translation).
(Continued)

*Primary Examiner* — Kevin Joyner
*Assistant Examiner* — Changru Chen
(74) *Attorney, Agent, or Firm* — Burr Patent Law, PLLC

(57) ABSTRACT

A method of cleaning and sterilizing a drink filling apparatus including a CIP process of circulating a cleaner in a drink supply piping to remove foreign matter on an interior of the drink supply piping, and an SIP process of sterilizing the interior of the drink supply piping. The processes are performed at the same time or in sequence without an interruption between the two. The SIP process uses the cleaner to sterilize the interior of the drink supply piping. After the SIP process, while the cleaner is kept circulating, a temperature condition at a predetermined position in the drink supply piping is adjusted to a temperature setting for manufacture, after which the cleaner in the drink supply piping is removed.

2 Claims, 8 Drawing Sheets

(56) References Cited

U.S. PATENT DOCUMENTS

| | | | |
|---|---|---|---|
| 2016/0121376 A1* | 5/2016 | Hayakawa | ................ B08B 3/10 422/3 |
| 2018/0178258 A1 | 6/2018 | Soellner et al. | |
| 2018/0334372 A1 | 11/2018 | Hayakawa et al. | |
| 2020/0277178 A1 | 9/2020 | Hayakawa et al. | |

FOREIGN PATENT DOCUMENTS

| | | |
|---|---|---|
| JP | 6131999 B | 5/2017 |
| JP | 2017-113575 A | 6/2017 |
| JP | 2017-114496 A1 | 6/2017 |
| JP | 2017-114569 A | 6/2017 |
| JP | 2019-064722 A1 | 4/2019 |
| WO | 2017/081155 A1 | 5/2017 |

OTHER PUBLICATIONS

International Search Report and Written Opinion (Application No. PCT/JP2018/036975) dated Jan. 8, 2019 (9 pages).

* cited by examiner

METHOD OF CLEANING AND STERILIZING DRINK FILLING APPARATUS

TECHNICAL FIELD

The present invention relates to a method of cleaning and sterilizing a drink filling apparatus that fills a container such as a PET bottle with a drink as a product.

BACKGROUND ART

When a drink filling apparatus fills a container such as a bottle with a product such as a drink, not only does a product sterilization process in which the product itself is sterilized to be aseptic have to be performed, but also the interior of product supply piping including a surge tank, a liquid feeding pipe, and filling nozzles in the drink filling apparatus has to be cleaned and sterilized to be aseptic in advance.

Conventionally, with regard to the drink itself flowing in the drink supply piping, the F value, which is a sterilization value, of the product is measured, and it is checked based on the historical information on the F value whether or not the product is sterilized to such an extent that the quality of the product can be assured (see Patent Document 1, for example).

With the drink supply piping of the drink filling apparatus, a CIP (Cleaning in Place) process and an SIP (Sterilizing in Place) process are performed regularly or each time the kind of drink is changed (see Patent Document 2, for example).

The CIP process is performed by passing a cleaner containing water and an alkali agent such as caustic soda as an additive through a flow path from the pipe line of the drink supply piping to the filing nozzles of the filling machine and then passing a cleaner containing water and an acid agent as an additive. The CIP process is performed by circulating the cleaner in the drink supply piping while a heating sterilization part is keeping the cleaner at 80° C., for example. The CIP process removes a residue of the previous product in the product supply piping, for example (see Patent Document 2, for example).

The SIP process is a process to sterilize the interior of the drink supply piping before the product filling operation is started, and is performed by passing a heated steam or hot water through the drink supply piping cleaned by the CIP process described above, for example. The heated steam or hot water is kept at 130° C., for example. The SIP process sterilizes the interior of the drink supply piping and makes it aseptic (see Patent Document 2, for example).

When the product is passed through the drink supply piping after the CIP process and the SIP process are performed, a product sterilization process is performed by heating and sterilizing the product in a heating sterilization part (UHT: Ultra High-temperature) arranged along the drink supply piping. Then, a container such as a bottle can be filled with the sterilized product (see Patent Document 1, for example).

PRIOR ART DOCUMENT

Patent Document

Patent Document 1: Japanese Patent Laid-Open No. 2007-215893

Patent Document 2: Japanese Patent Laid-Open No. 2007-22600

DISCLOSURE OF THE INVENTION

Problems to be Solved by the Invention

By performing cleaning and sterilization of the drink filling apparatus and sterilization of the product in the manner described above, the quality of the product can be properly and quickly assured.

However, according to a sterilization method that performs different processes such as the CIP process, the SIP process and the product sterilization process on the drink supply piping of the drink filling apparatus, when transitioning from the CIP process to the SIP process, a rinsing process is performed to rinse the cleaner used in the CIP process with aseptic water at room temperature. Therefore, as shown in FIG. 8, the temperature of the heating sterilization part decreases and thus needs to be raised to a temperature for the SIP process before the SIP process is started. Thus, there is a problem that the CIP process and the SIP process and the transition between the processes take a very long time. Furthermore, there is another problem that a switching operation including change of the UHT holding tube (swing bend), replacement and inspection of filters at different positions, and disassembly and cleaning of the homogenizer is performed between the CIP process and the SIP process and between the manufacturing step and the CIP process, and the switching operation takes a very long time.

As described above, according to the conventional cleaning and sterilization method, products cannot be manufactured during the CIP process or the SIP process, so that the operation rate of the drink filling apparatus decreases, and the products cannot be efficiently manufactured. There is an intense demand for solving these problems.

The present invention has been devised to solve these problems, and an object of the present invention is to provide a method and an apparatus of cleaning and sterilizing a drink filling apparatus that can efficiently manufacture products with an increased operation rate.

Means for Solving the Problems

A method of cleaning and sterilizing a drink filling apparatus according to the present invention is a method of cleaning and sterilizing a drink filling apparatus that includes drink supply piping that feeds a product into a filling machine through a heating sterilization part, the method comprising a CIP process of circulating a cleaner in the drink supply piping to remove a remaining foreign matter from a product or the like on an interior of the drink supply piping and an SIP process of sterilizing the interior of the drink supply piping, wherein the CIP process and the SIP process are performed at the same time or in sequence without an interruption between the CIP process and the SIP process, the SIP process uses the cleaner circulating in the drink supply piping to sterilize the interior of the drink supply piping, a temperature condition at a predetermined position in the drink supply piping is adjusted to a predetermined temperature while the cleaner is kept circulating after the SIP process, and after the temperature condition at the predetermined position in the drink supply piping is adjusted to the predetermined temperature, the cleaner in the drink supply piping is removed.

In the method of cleaning and sterilizing a drink filling apparatus according to the present invention, the cleaner in the drink supply piping is preferably removed by flowing aseptic water in the drink supply piping.

Effects of the Invention

According to the present invention, the CIP process using the cleaner is followed by the SIP process without stopping the liquid feeding pump, the cleaner used for the CIP process is also used for the SIP process, and after the SIP process, while the cleaner is still circulating, the temperature condition at a predetermined position in the drink supply piping is adjusted to the temperature setting for manufacture, and then the cleaner is removed by rinsing the interior of the drink supply piping with aseptic water. Therefore, the time required for transition from the CIP process to the SIP process can be reduced. In addition, since the temperature condition of the drink supply piping is adjusted to the temperature condition for manufacture before removing the cleaner by rinsing, the drink filling apparatus can be sterilized without major modifications to the drink filling apparatus.

BEST MODE FOR CARRYING OUT THE INVENTION

In the following, an embodiment of the present invention will be described with reference to the drawings.

A configuration of a drink filling apparatus will be first described, and a method of cleaning and sterilizing the apparatus and a product filling method for the apparatus will then be described.

Figure 1:
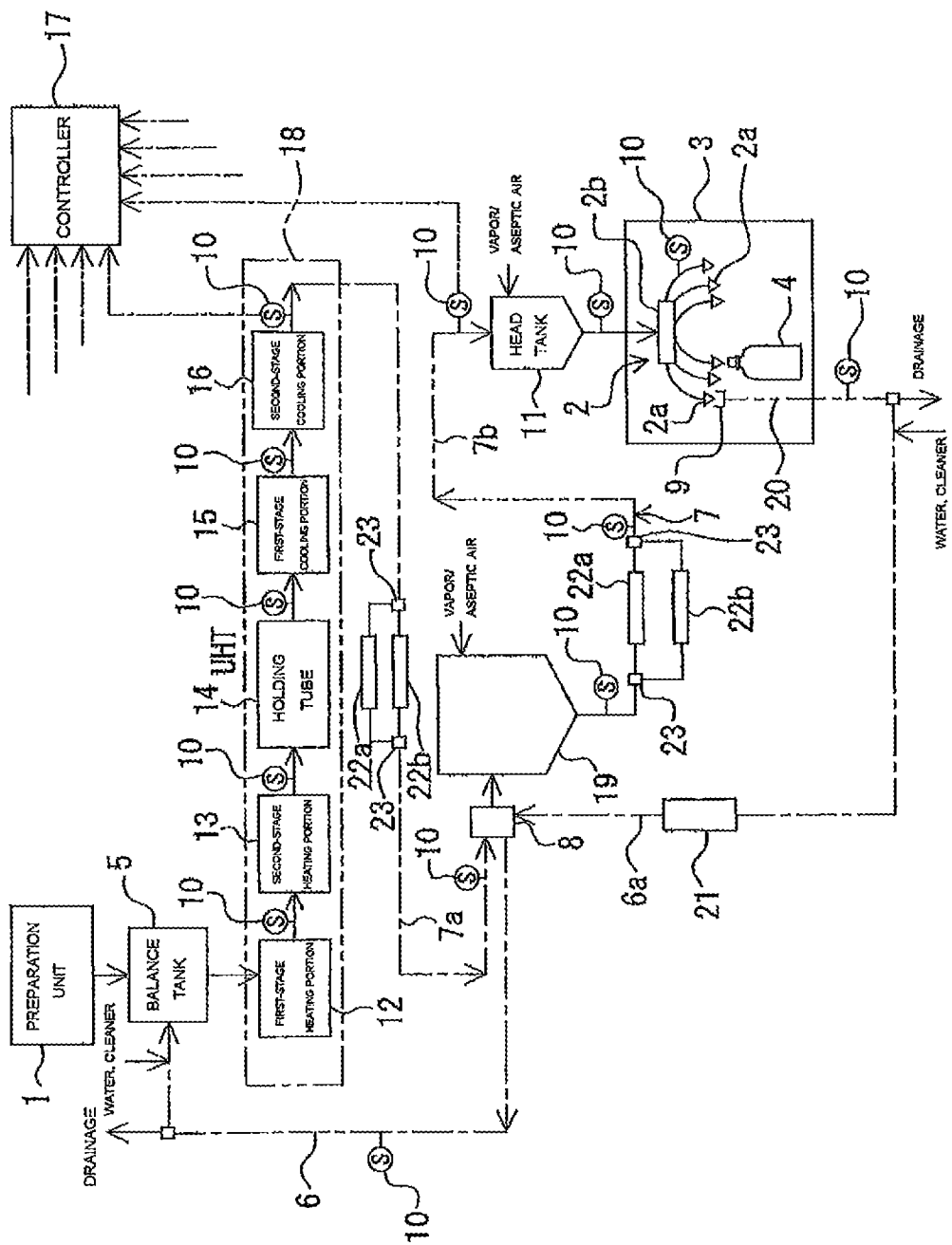
FIG. 1 is a block diagram showing a drink filling apparatus to which a cleaning and sterilization method according to the present invention is applied.

As shown in FIG. 1, the drink filling apparatus includes a preparation unit 1 for a drink as a product and a filling machine 2 that fills a bottle 4 with the drink. The preparation unit 1 and filling nozzles 2a in the filling machine 2 are coupled to each other by drink supply piping 7. The filling machine 2 is surrounded by an aseptic chamber 3.

The preparation unit 1 prepares a drink such as tea or fruit juice by mixing ingredients in desired proportions. The preparation unit 1 is a well-known device and therefore will not be described in detail herein.

The filling machine 2 includes a large number of filling nozzles 2a arranged around a wheel (not shown), which rotates at high speed in a horizontal plane. This is a machine for filling a certain amount of the drink from the filling nozzle 2a into each bottle 4 traveling below the filling nozzles 2a at a velocity adjusted to the circumferential velocity of the wheel. The filling machine 2 is also a well-known machine and therefore will not be described in detail herein.

In the drink filling apparatus, along the path of the drink supply piping 7 from the preparation unit 1 to the filling machine 2, a balance tank 5, a heating sterilization part (hereinafter, referred to as UHT: Ultra High-temperature) 18, a manifold valve 8, an aseptic surge tank 19, and a head tank 11 are disposed in this order from upstream to downstream of the flow of the drink.

The UHT 18 includes a first-stage heating portion 12, a second-stage heating portion 13, a holding tube 14, a first-stage cooling portion 15 and a second-stage cooling portion 16, for example. The drink or water supplied from the balance tank 5 is gradually heated while fed from the first-stage heating portion 12 to the second-stage heating portion 13 until a target sterilization temperature is reached at an exit of the second-stage heating portion 13, kept at the sterilization temperature for a certain time in the holding tube 14, and then gradually cooled while fed from the first-stage cooling portion 15 to the second-stage cooling portion 16. The number of stages of heating portions or cooling portions can be increased or decreased as required. The UHT 18 may include a homogenizer capable of automatic washing. The homogenizer is preferably disposed between the first-stage heating portion and the second-stage heating portion or between the first-stage cooling portion and the second-stage cooling portion where the temperature of the content of the product is about 50 to 70° C. In the former case, a common homogenizer can be used. In the latter case, however, an aseptic homogenizer is needed.

The balance tank 5, the manifold valve 8, the aseptic surge tank 19 and the head tank 11 are well-known devices and therefore will not be described in detail herein.

Figure 2:
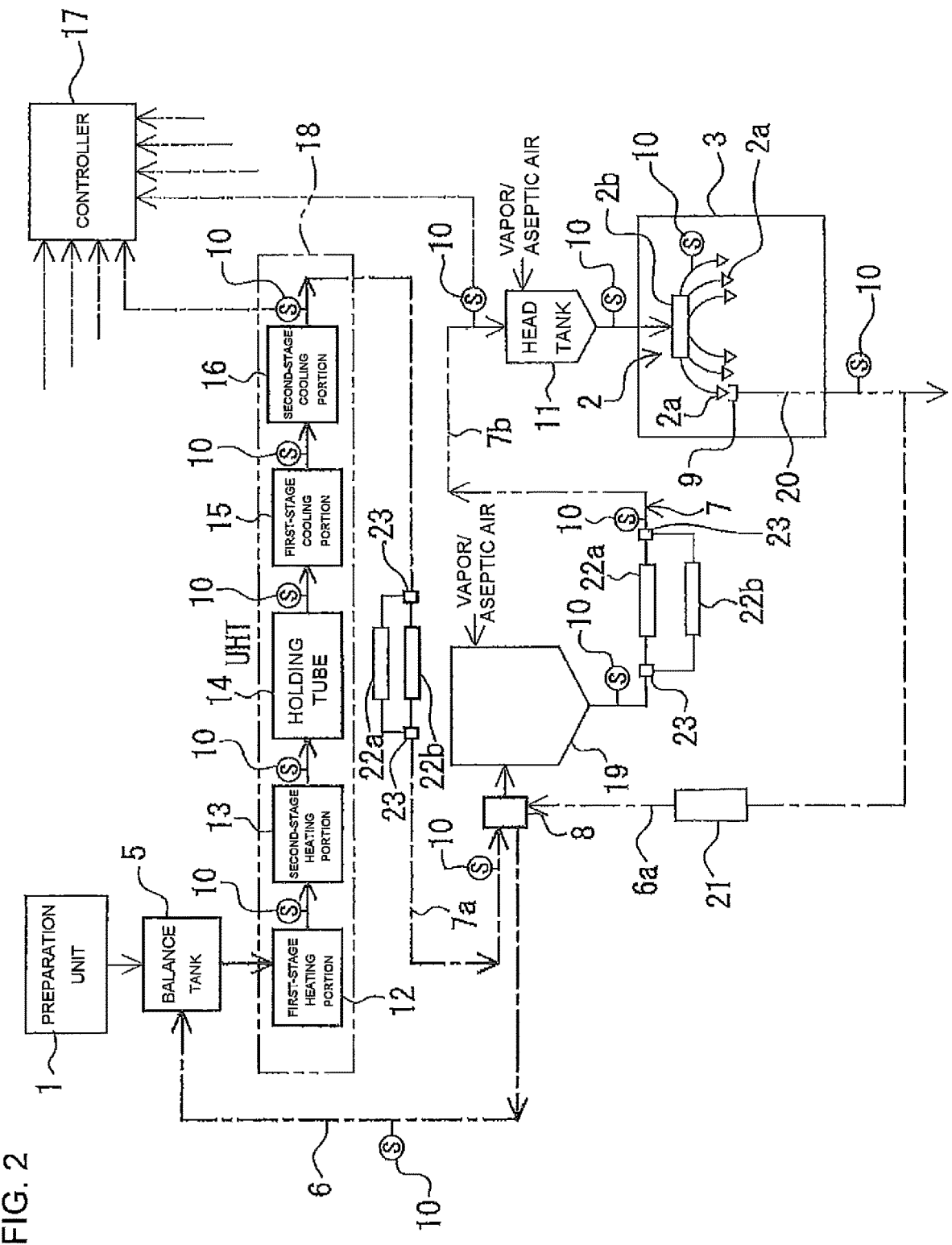
FIG. 2 is a block diagram for illustrating a CIP process or STP process performed for an upstream-side piping section of a drink supply piping from a heating sterilization part (inclusive) to a position just before an aseptic surge tank (ACT) (exclusive) in the cleaning and sterilization method according to the present invention.

Next, a process path along which a CIP process and an SIP process are performed will be described. As shown by a bold line in FIG. 2, an upstream-side piping section 7a of the drink supply piping 7, which extends from the balance tank 5 to the manifold valve 8 through the UHT 18, is provided with a feedback path 6 to form an upstream-side process path, which is a circulation path for the CIP process or SIP process. As shown by a bold line in FIG. 3, a downstream-side piping section 7b, which extends from the manifold valve 8 to the aseptic surge tank 19, then to the head tank 11, then to the filling machine 2 and then back to the manifold valve 8, is provided with a feedback path 6a to form a downstream-side process path, which is a circulation path for the CIP or SIP process.

The upstream-side piping section 7a is provided with temperature sensors 10 at positions including a position where the temperature is less likely to increase when hot water or the like is supplied to the interior thereof. For example, the temperature sensors 10 can be disposed at positions along the pipe line from the first-stage heating portion in the UHT 18 to the manifold valve 8, such as positions in the UHT 18, a position at the outlet of the second-stage cooling portion 16, and a position at the inlet of the manifold valve 8. The temperature sensors 10 are disposed at these positions. Temperature information from the temperature sensors 10 is transmitted to a controller 17.

The balance tank 5 can be any tank, such as an open tank for which the filling temperature is prescribed to be lower than 100° C. or a tank that is a first class pressure vessel to which a fluid at a temperature of 100° C. or higher can be fed. When the open tank is used, a cooling unit is preferably provided between the manifold valve 8 and the balance tank 5.

Figure 3:
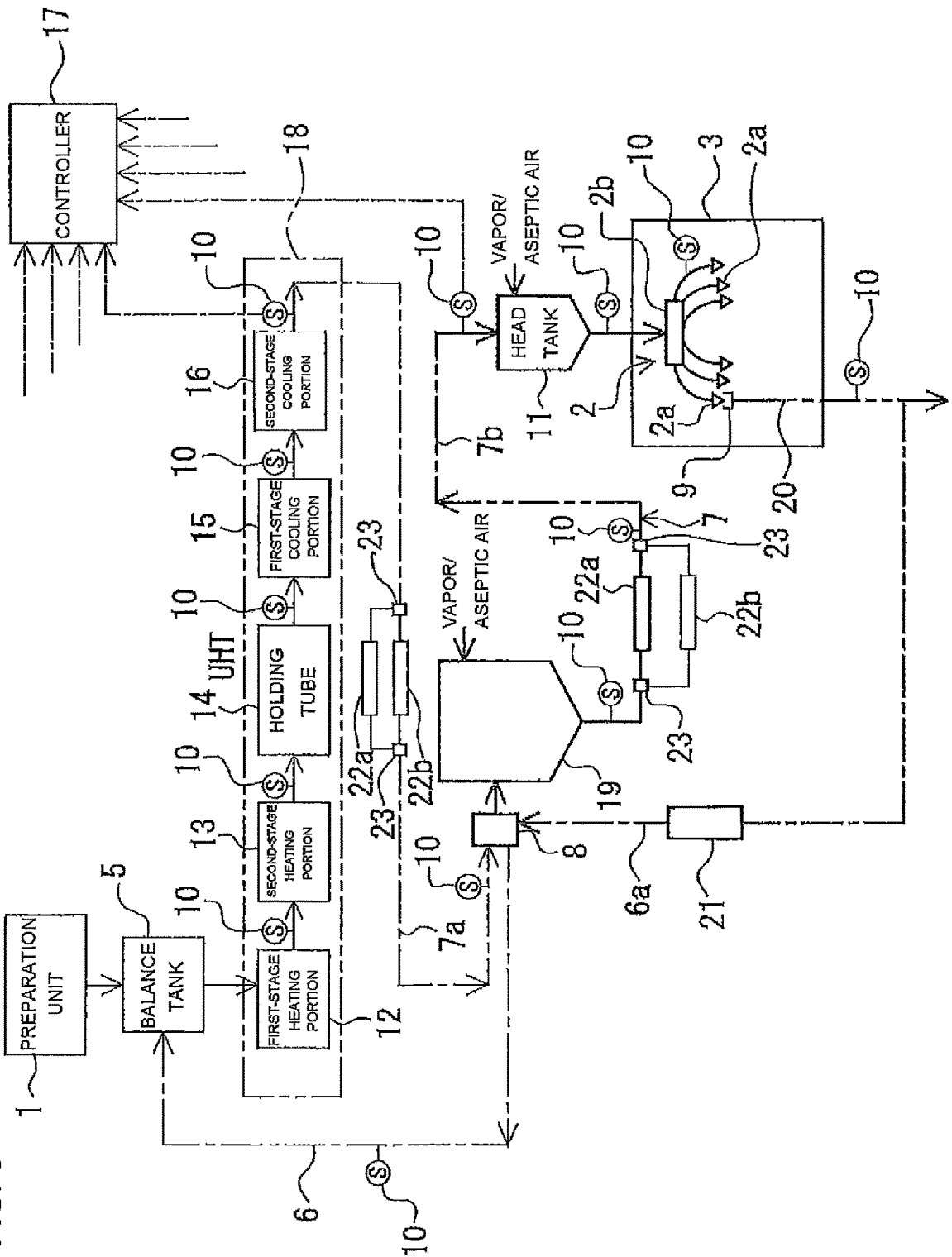
FIG. 3 is a block diagram for illustrating the CIP process or SIP process performed for a downstream-side piping section of the drink supply piping from the aseptic surge tank (inclusive) to filling nozzles (inclusive) in the cleaning and sterilization method according to the present invention.

As shown by the bold line in FIG. 3, the downstream-side piping section 7b of the drink supply piping 7, which is located downstream of the upstream-side piping section 7a and extends from the manifold valve 8 to the filling machine 2 through the aseptic surge tank 19 and the head tank 11, is also provided with temperature sensors 10 at positions including a position where the temperature is less likely to increase when heated steam or the like is supplied to the interior thereof. For example, the temperature sensors 10 can be disposed at positions along the pipe line from the aseptic surge tank 19 to the filling nozzles 2a, such as a position in the vicinity of the outlet of the aseptic surge tank 19, a midway bent point, positions in the vicinities of the inlet and outlet of the head tank 11, positions between a manifold 2b and the filling nozzles 2a in the filling machine 2. The temperature sensors 10 are disposed at these positions. Temperature information from the temperature sensors 10 is transmitted to the controller 17.

In the downstream-side piping section 7b, a cup 9 is provided for an opening of each filling nozzle 2a in the filling machine 2 for the CIP process or SIP process, and the cup 9 can be brought closer to and separated from the filling nozzle 2a. To perform the CIP process or SIP process, an actuator (not shown) puts each cup 9 on the opening at the tip end of the filling nozzle 2a in the filling machine 2 to connect a leading end of a drain tube 20 to the opening of the filling nozzle 2a.

The drink supply piping 7 can include various switching valves, liquid feeding pumps or other components in addition to the manifold valve 8 and the actuator (not shown), and these components are also controlled by the controller 17.

Figure 4:
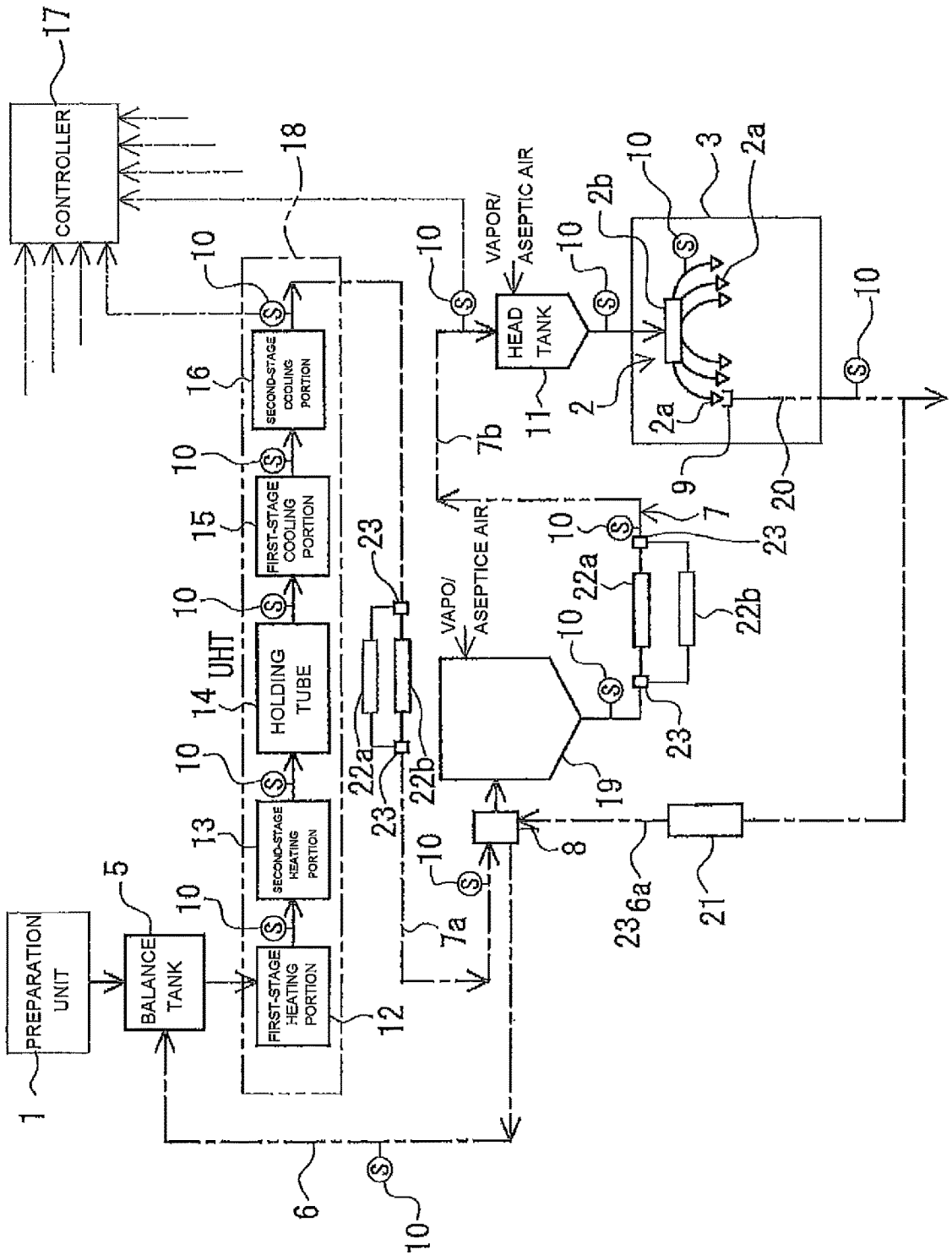
FIG. 4 is a block diagram for illustrating the CIP process performed for the entire drink supply piping in the cleaning and sterilization method according to the present invention.

The CIP process or the SIP process may not be separately performed for the upstream-side piping section 7a and the downstream-side piping section 7b, and as shown by the bold line in FIG. 4, the process path may be formed by the drink supply piping 7 including the balance tank 5, the UHT 18, the manifold valve 8, the aseptic surge tank 19, the head tank 11 and the filling machine 2 and the circulation path from the filling machine 2 to the balance tank 5.

Next, a cleaning and sterilization method for the drink filling apparatus described above and a method of transition from the CIP process to the SIP process will be described with reference to FIGS. 2 to 6.

(CIP Process)

When an operation button on a panel (not shown) of the controller 17 is manipulated, the CIP process is performed for each of the upstream-side piping section 7a and the downstream-side piping section 7b of the drink supply piping 7 in a predetermined procedure. The CIP process is performed by flowing an alkali cleaner that contains a mixture of water and an alkali agent such as caustic soda (sodium hydroxide), potassium hydroxide, sodium carbonate, sodium silicate, sodium phosphate, sodium hydrochloride, a surface active agent or a chelating agent (sequestering agent) such as sodium gluconate or ethylenediaminetetraacetic acid (EDTA) and is supplied from a cleaner supply source (not shown) and then flowing an acid cleaner that contains a mixture of water and a nitrate-based or phosphate-based acid agent and is supplied from a cleaner supply source (not shown).

The alkali cleaner may include lithium carbonate, ammonium carbonate, magnesium carbonate, calcium carbonate, propylene carbonate or a mixture thereof. However, the alkali cleaner is not limited to those substances. For example, the alkali cleaner may include bicarbonate such as sodium bicarbonate, potassium bicarbonate, lithium bicarbonate, ammonium bicarbonate, magnesium bicarbonate or calcium bicarbonate, sesquicarbonate such as sodium sesquicarbonate, potassium sesquicarbonate or lithium sesquicarbonate, or a mixture thereof.

The acid cleaner may include, in addition to above described the nitric acid or phosphoric acid, hydrochloric acid, sulfuric acid, acetic acid, citric acid, lactic acid, formic acid, glycolic acid, methanesulfonic acid, sulfamic acid or a mixture thereof. However, the acid cleaner is not limited to those substances.

The cleaner may include various bleaching agents such as hypochlorite, hydrogen peroxide, peracetic acid, peroctanoic acid, persulfate, perborate, hydrosulfite or thiourea dioxide, or percarbonate, for example. The detergents may further include a water softener such as aluminosilicate or polycarboxylate, or an antiredeposition agent such as sodium phosphate, sodium polyacrylate or sodium carboxylate. Furthermore, the cleaners may include an enzyme, a solvent, a fatty acid, a deformer, an active oxygen source or the like.

The cleaners can be used in other sequences than the sequence described above in the CIP process. For example, the alkali cleaner may be used after the acid cleaner is used, or only one of the acid cleaner and the alkali cleaner may be used for cleaning.

The cleaners supplied from the cleaner supply sources (not shown) are activated by the UHT 18 provided for the upstream-side piping section 7a and the heating unit 21 provided for the downstream-side piping section 7b until a predetermined flowrate (1.5 m/s or higher, for example) and a predetermined temperature (80° C., for example) are reached. The cleaners are constantly or intermittently supplied in a constant amount from the respective cleaner supply sources (not shown) and remove drink residues from the previous operation on the interior of the drink supply piping 7 while circulating in the drink supply piping 7. The cleaners may be discharged from the apparatus as appropriate. After the cleaners are passed for a predetermined time, the CIP process ends. The completion of the CIP process is managed by the controller 17, and then transition to the SIP process occurs.

(SIP Process)

When the CIP process ends, the SIP process is performed for each of the upstream-side process path and the downstream-side process path in a predetermined procedure. Before the SIP process is started, the manifold valve 8 disconnects the upstream-side piping section 7a and the downstream-side piping section 7b from each other as required.

The SIP process for the upstream-side process path and the SIP process for the downstream-side process path can be performed in sequence or in parallel with each other.

First, the SIP process for the upstream-side process path will be described. The liquid feeding pump used for the CIP process is not stopped, and while the cleaner used in the CIP process is circulating in the upstream-side piping section 7a, the cleaner is heated and sterilized in the UHT 18 while circulating in the circulation path. In this way, the interior of the upstream-side process path is sterilized. In this step, since the liquid feeding pump is not stopped, the temperature of the UHT 18 raised and set in the CIP process does not decrease but is further raised to a temperature for the SIP process. Thus, the temperature drop during transition from the CIP process to the SIP process can be minimized (see FIG. 6).

When the cleaner is flowing in the upstream-side process path, the temperature sensors 10 disposed at different positions along the upstream-side piping section 7a transmit temperature information to the controller 17 at regular time intervals. In this embodiment, it is assumed that the drink, which is a product liquid with which the bottle 4 is filled, has a pH of 4.6 or higher and a reference temperature Tr is 121.1° C., and the Z value is 10° C.

When the temperature at each of the different positions raised by heating by the cleaner reaches 121.1° C., the controller 17 starts calculating the F value at the position according to the following formula.

$$F = \int_{t_0}^{t_1} 10^{(T-121.1)/10} dt \qquad \text{[formula 1]}$$

where T denotes an arbitrary sterilization temperature (° C.), $10^{(T-121.1)/10}$ represents a fatality rate at an arbitrary temperature T and corresponds to a heating duration (in minutes) at 121.1° C., which is a reference temperature, and 10 denotes a Z value (° C.).

When the minimum F value of the F values calculated according to the formula described above reaches a target value, it is determined that sterilization of the upstream-side piping section 7a is completed. The sterilization method is not limited to the sterilization method based on the calculated F value described above but may be a known sterilization method based on temperature and time, for example.

Figure 6:
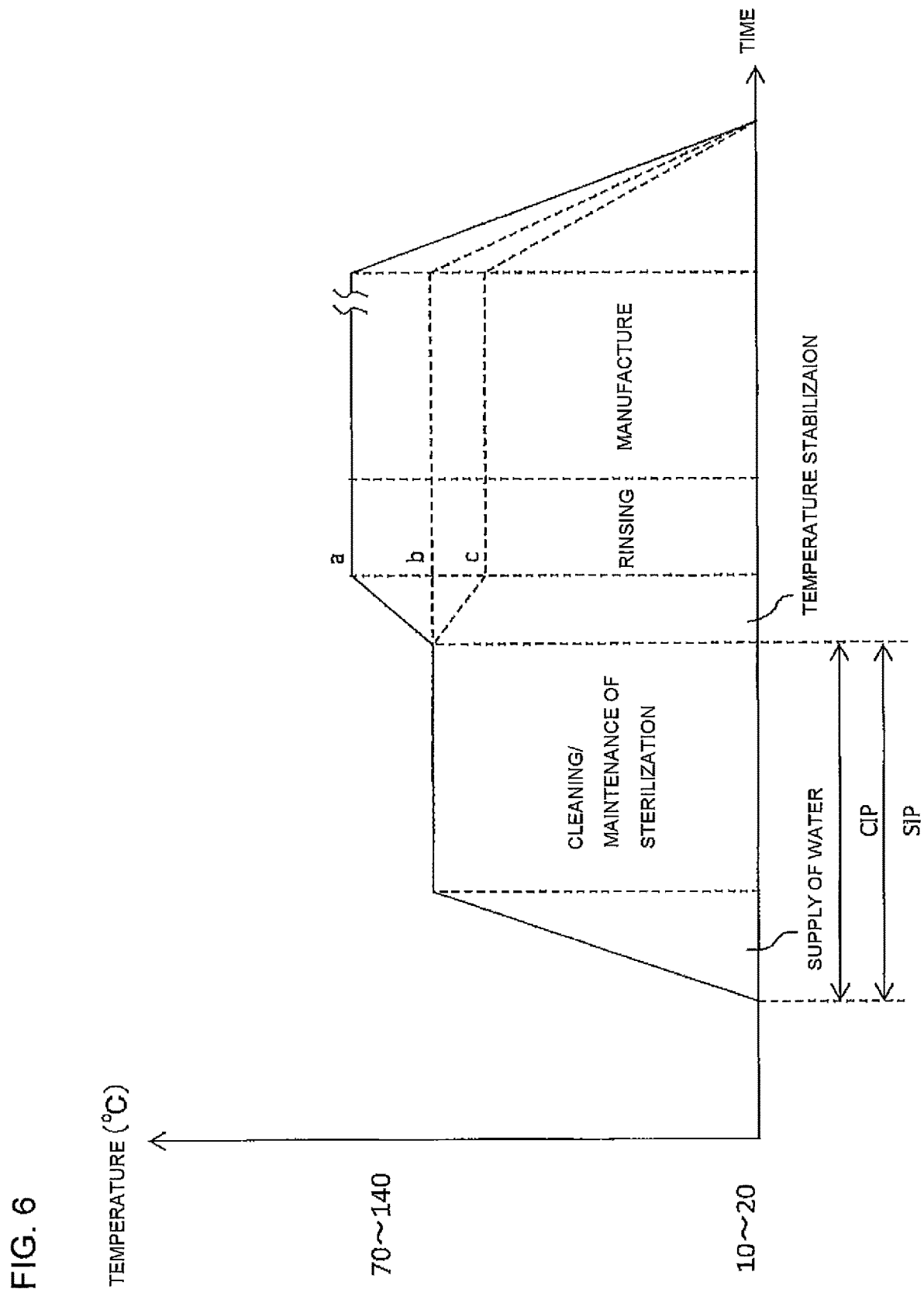
FIG. 6 is a graph for illustrating a variation in temperature of the upstream-side piping section in the CIP process, the SIP process and a manufacturing step in the cleaning and sterilization method according to the present invention.

As shown in FIG. 6, while the cleaner is kept circulating in the upstream-side piping section 7a, the temperature condition of the UHT 18 is set at a temperature condition for manufacture (see a to c in FIG. 6). In the temperature stabilization step, again, the F value is constantly calculated according to the formula described above and controlled to prevent reduction of the sterilization strength. After that, the aseptic water is supplied to the upstream-side piping section 7a to remove the cleaner in the upstream-side piping section 7a. In this step, if water (preferably pure water) is supplied to the upstream-side piping section 7a, and the F value is controlled to prevent reduction of the sterilization strength based on the temperature and flowrate of the water measured by the temperature sensor 10 immediately after the holding tube 14 in the UHT 18, no additional aseptic water supply apparatus is needed, and since the water is heated in the UHT 18, the supplied water can be made aseptic and the interior of the drink supply piping can be kept aseptic. After that, when the cleaner in the upstream-side piping section 7a is completely replaced with the aseptic water or the water that has been made aseptic, the supply of the aseptic water or the water is stopped, while the aseptic water is kept continuously circulating while waiting for the start of sterilization of the drink. In the temperature stabilization step, in addition to setting the UHT 18 at the same temperature condition as the temperature condition for manufacture, the temperature of the first-stage cooling portion 15 and the second-stage cooling portion 16 may be set at a temperature (lower than 100° C., for example) higher than the temperature according to the manufacturing condition, and the each of the set temperatures may be adjusted to the temperature according to the manufacturing condition during waiting while continuously circulating the aseptic water.

In the temperature stabilization step, the sterilization temperatures at the positions in the UHT 18 and the time required for the water to pass through the holding tube 14 are recorded at intervals of 1 second. The temperature data and the flowrate data are transmitted to the controller 17 and stored. The temperature data and the flowrate data are preferably recorded for a period of time (for example, 200 seconds) that is three or four times as long as the passing time of the holding tube 14 (for example, 60 seconds), because such a length of time allows calculation of the actual strength of the sterilization of the content having passed through the holding tube 14.

If the pressure of the drink passing through the UHT 18 is lower than the pressure of the heat source that heats the UHT 18 or the coolant that cools the UHT 18, poor sterilization can occur. From the viewpoint of safe back pressure, the pressure of the drink passing through the UHT 18 is adjusted and set to be greater than the pressure of the heat source that heats the UHT 18 or the coolant that cools the UHT 18.

In the formula for calculating the F value described above, the reference temperature Tr and the Z value can be changed according to the kind of the drink, which is a product liquid.

For example, when the pH of the product liquid is equal to or higher than 4 and lower than 4.6, the reference temperature Tr can be 85° C., and the Z value can be 7.8° C. When the pH of the product liquid is lower than 4, the reference temperature Tr can be 65° C., and the Z value can be 5° C.

The values to be substituted into the formula described above can be changed as appropriate according to the ease of development of microorganisms, the temperature during distribution or the like of the product liquid, such as tea, mineral water or a chilled drink.

When or before the SIP process for the upstream-side piping section 7a is started, the SIP process for the downstream-side process path including the aseptic surge tank 19 is started.

Next, the SIP process for the downstream-side process path will be described. First, the cups 9 are placed over the openings of the filling nozzles 2a to connect the drain tubes 20 to the filling nozzles 2a, and then, if the upstream-side piping section 7a and the downstream-side piping section 7b are not disconnected, the cleaner used in the CIP process is circulated. When the cleaner is flowing in the downstream-side piping section 7b, the temperature sensors 10 disposed at different positions transmit temperature information to the controller 17 at regular time intervals. F values are calculated based on the information, and the controller 17 determines whether or not the minimum F value of the calculated F values has reached a target value.

Besides, a flowrate sensor attached to each filling nozzle 2a transmits flowrate information to the controller 17 at regular time intervals. The relationship between the flowrate of the cleaner passing through each filling nozzle 2a and the sterilization effect of the filling nozzle 2a is experimentally determined in advance. Based on the result of the experiment, the controller 17 determines whether or not the minimum flowrate of the flowrates for all the filling nozzles 2a has reached a target value.

The controller 17 monitors the flowrates of the cleaner through the filling nozzles 2a based on the flowrate information from the flowrate sensors and monitors a representative temperature of at least one filling nozzle 2a based on the temperature information from the temperature sensor 10. When both the flowrate and the representative temperature reach the respective target values, the controller 17 ends the sterilization process. After that, the temperature condition of the UHT 18 is set at the temperature condition for manufacture in the temperature stabilization step for the upstream-side piping section 7a, the cleaner in the downstream-side piping section 7b is removed with the supplied aseptic water or the water made aseptic in the UHT 18, and when the cleaner in the downstream-side piping section 7b is completely replaced with the aseptic water or the water made aseptic, the supply of the aseptic water or the water is stopped. At the same time, in order to prevent lowering of the positive pressure in the piping, aseptic air is supplied into the tanks and the piping to keep the interior of the sterilized piping at a positive pressure.

When the SIP process for the downstream-side piping section 7b is separately performed by disconnecting the upstream-side piping section 7a and the downstream-side piping section 7b from each other, a heated steam or hot water is supplied from a supply source (not shown) into the aseptic surge tank 19 and the head tank 11.

The heated steam or hot water flows from the aseptic surge tank 19 to the filling nozzles 2a through the downstream-side piping section 7b and heats the components along the way before being discharged out of the filling machine 2 through the drain tubes 20. As required, a heat exchanger that exchanges heat with the water flowing out of the drain tubes 20 may be arranged between the drain tubes 20 and a heating unit 21. In this way, the downstream-side piping section 7b is sterilized by the warm water or hot water.

While the heated steam or hot water is flowing in the downstream-side piping section 7b, the temperature sensors 10 disposed at different positions in the downstream-side piping section 7b transmit temperature information to the controller 17 at regular time intervals.

When the temperature raised by heating by the heated steam or hot water reaches 121.1° C. at each position, the controller 17 starts calculating the F value at the position according to the formula described above.

When the minimum F value of the calculated F values reaches a target value, supply of the heated steam or hot water to the aseptic surge tank 19 and the interior of the downstream-side piping section 7b is stopped. The time required for the SIP for the downstream-side piping section 7b is substantially reduced compared with the conventional SIP process.

Thereafter, aseptic air, aseptic water or the product is fed into the downstream-side piping section 7b to cool the interior of the downstream-side piping section 7b to, for example, room temperature. Then, the drain tubes 20 are disconnected. Furthermore, the actuator (not shown) removes the cups 9 from the openings of the filling nozzles 2a. The aseptic water may be fed from the product sterilizer that has finished the SIP process for the downstream-side process path and is in the water operation in the standby state. Alternatively, aseptic water (not shown) may be received through the manifold valve 8 and used for cooling. The cooling with the aseptic water can be started after the temperature of the tank after the SIP process has been reduced to below 110° C. (preferably to below 100° C.) by cooling with the aseptic air. The operation of supplying the aseptic water is performed under pressure by supplying aseptic air to prevent the pressure in the tank from decreasing due to rapid cooling by using an intermittent timer. After the temperature of the tank has decreased to about 30 to 90° C., and the cooling is completed, the aseptic water remaining in the tank and the piping is blown off by aseptic air while maintaining a positive pressure, and the product is received.

Alternatively, the cooling with the aseptic water may be omitted, and the product may be received immediately after the SIP process. By additionally using the aseptic water or the product for cooling as described above, the cooling can be achieved in a shorter time than when only air is used for cooling. The tank may be quickly cooled by supplying water or chiller water to a jacket of the tank in parallel with the cooling process described above. In the cooling step with the aseptic air in the SIP process, the blow valves may be sequentially closed at positions where the cooling completion temperature is reached to efficiently feed the cooling aseptic air to parts that are more difficult to cool.

If the drink to be manufactured next is a carbonated drink, the aseptic water is fed from a vicinity of the aseptic surge tank 19 to the head tank 11 and the filling nozzles 2a through a carbonated drink line (not shown). On the carbonated drink line, the aseptic water is further cooled (to 1 to 5° C.) by chiller water. Thus, the remaining heat from the SIP process can be completely removed, and foaming of the carbon dioxide gas can be reduced during filling.

As with the case of the upstream-side piping section described above, transition from the CIP process to the SIP process can be performed while increasing the temperature from the temperature at which the CIP process has been performed to the temperature at which the SIP process is to be performed.

To perform the SIP process for one of the upstream-side process path and the downstream-side process path while performing the CIP process for the other, a valve unit (with a vapor barrier) that allows steam to pass therethrough is preferably provided at an intersection between both the paths in the manifold valve 8. In that case, even if a valve fails on one of the process paths, the risk of contamination of the interior of the other path is reduced. Alternatively, aseptic water can be used instead of the steam, or risks that may occur when a valve fails can be reduced by arranging a plurality of valves at the intersection of the process paths.

(Manufacturing Step)

After the SIP process for the aseptic surge tank 19 and the following part of the downstream-side piping section 7b ends, the drink flowing from the UHT 18 through the upstream-side piping section 7a is stored in the aseptic surge tank 19, and a manufacturing step of filling the bottles 4 with the drink flowing therefrom through the downstream-side piping section 7b is started.

Figure 5:
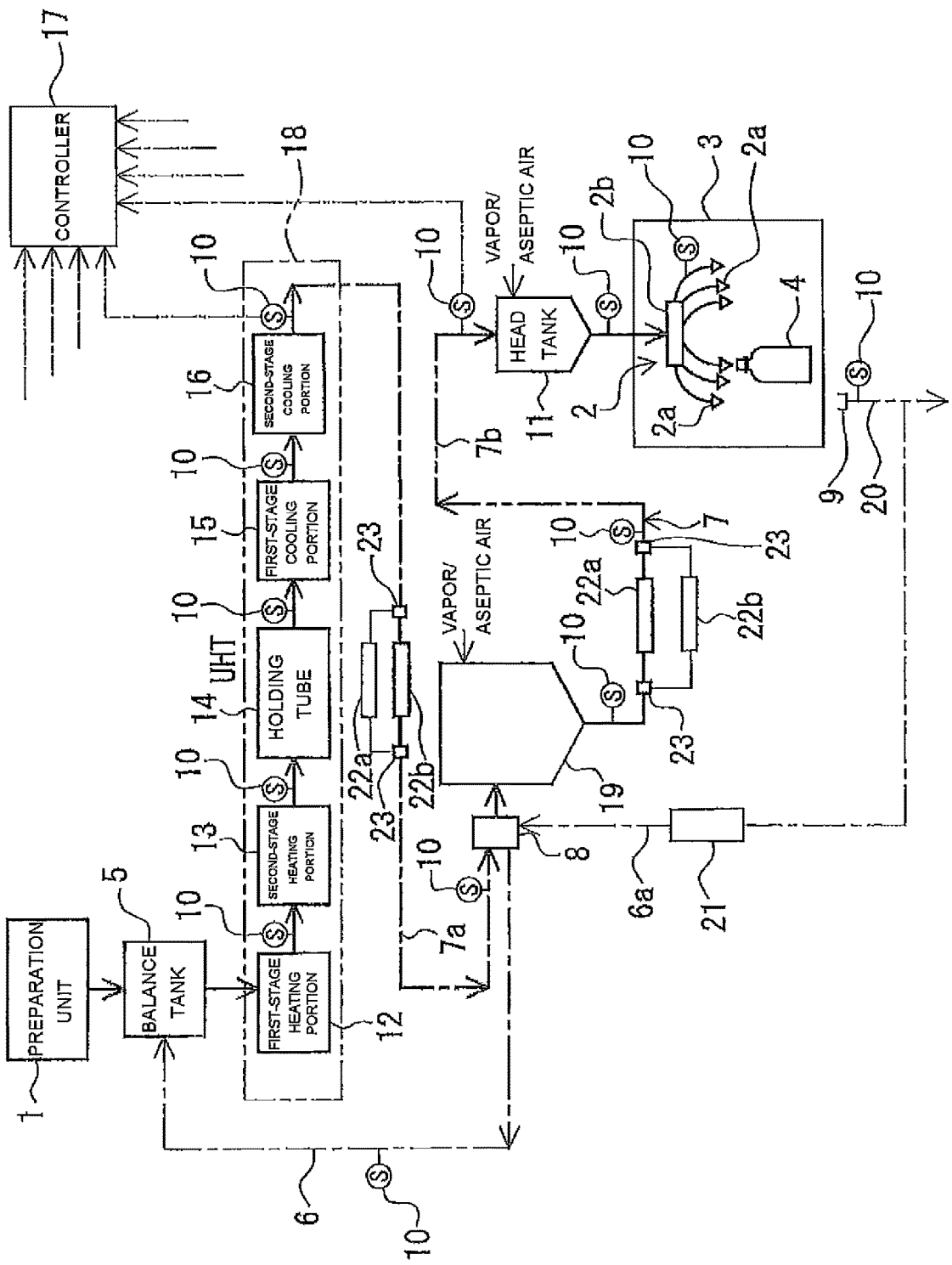
FIG. 5 is a block diagram for illustrating production of a bottled product.

As shown by a bold line in FIG. 5, in the manufacturing step, the drink prepared in the preparation unit 1 flows to the interior of the filling machine 2 through the sterilized upstream-side piping section 7a and downstream-side piping section 7b of the drink supply piping 7, and the bottles 4 as containers are filled with the product through the filling nozzles 2a in the filling machine 2. The bottles 4 filled with the drink are capped by a capper (not shown) and then fed out of the filling machine 2.

After the manufacturing step is completed, a second manufacturing step can be continuously performed to manufacture a different kind of product than the previous product. In that case, the drink supply piping 7 needs to be cleaned and sterilized in the same processes as the CIP and SIP processes described above. However, before starting the CIP process of the second manufacturing step, a transition from the set temperature of the UHT 18 in the first manufacturing step to the set temperature for the CIP process is preferably made while performing the rinsing process of passing water, aseptic water or the like through the drink supply piping 7.

The drink supply piping 7 is preferably provided with a filtering device that filters out foreign matters in the product.

The filtering device includes a first filtering device and a second filtering device arranged in parallel with each other, and the first and second filtering devices include a filtering member formed by a metal filter, such as a stainless steel filter. The filtering device further includes switching devices 23, 23 that automatically or manually switch between the first filtering device 22a and the second filtering device 22b.

The first filtering device 22a and the second filtering device 22b are preferably metal filters such as stainless steel filters and preferably differ in mesh fineness (mesh size). Preferably, for example, the first filtering device 22a includes a metal filter of 100 to 400 mesh capable of removing finer foreign matters, and the second filtering device 22b includes a rougher metal filter of 10 to 100 mesh capable of appropriately allowing flesh or pulp in the product to pass therethrough. By using filtering devices of different counts for the first filtering device 22a and the second filtering device 22b as described above, foreign matters can be appropriately removed from each individual product to be manufactured.

In addition, the switching devices 23, 23 allow switching between the first filtering device 22a and the second filtering device 22b. Since the switching devices 23, 23 are provided, while the first filtering device 22a is being used for filling with the product as shown in FIG. 5, a cleaning step for the second filtering device 22b can be performed to remove foreign matters from the second filtering device 22b. Thus, during manufacture of the product, the filtering device can be efficiently cleaned and inspected. After the cleaning and inspection of the filters, the CIP process or the SIP process can be separately performed. The switching devices 23 can be set to feed liquid to both the first filtering device 22a and the second filtering device 22b. In that case, the CIP process or the SIP process for both the first filtering device 22a and the second filtering device 22b can be performed at the same time. To reduce the risk of contamination of the product by a chemical agent or bacteria, the vapor barrier described above may be provided in the switching devices 23.

As shown in FIG. 1, for example, the filtering device may be disposed between the second-stage cooling portion (final cooling portion) 16 and the manifold valve 8, rather than being disposed between the aseptic surge tank 19 and the head tank 11. A plurality of filtering devices arranged in parallel with each other may be provided. The filtering device may be disposed at different positions, for example, at a position upstream of the balance tank 5 or at the tip ends of the filling nozzles.

As described above, the first filtering device and the second filtering device are arranged in parallel with each other in the filtering device. Therefore, for example, filtering of the product can be performed by the first filtering device when the product is manufactured in the first manufacturing step, and can be performed by the second filtering device when the product is manufactured in the second manufacturing step. In that case, while the product is being manufactured, the filtering device that is not used for filtering of the product is preferably subjected to a cleaning step of removing remaining foreign matters from the manufacturing step and an inspection operation of checking that the product does not contain rubber or metal foreign matters such as a gasket residue. By performing the cleaning operation and the inspection operation during manufacture of the product as described above, a cleaned filtering device can always be used after transition from the first manufacturing step to the second manufacturing step, and the operation rate of the drink filling apparatus is improved.

Figure 7:
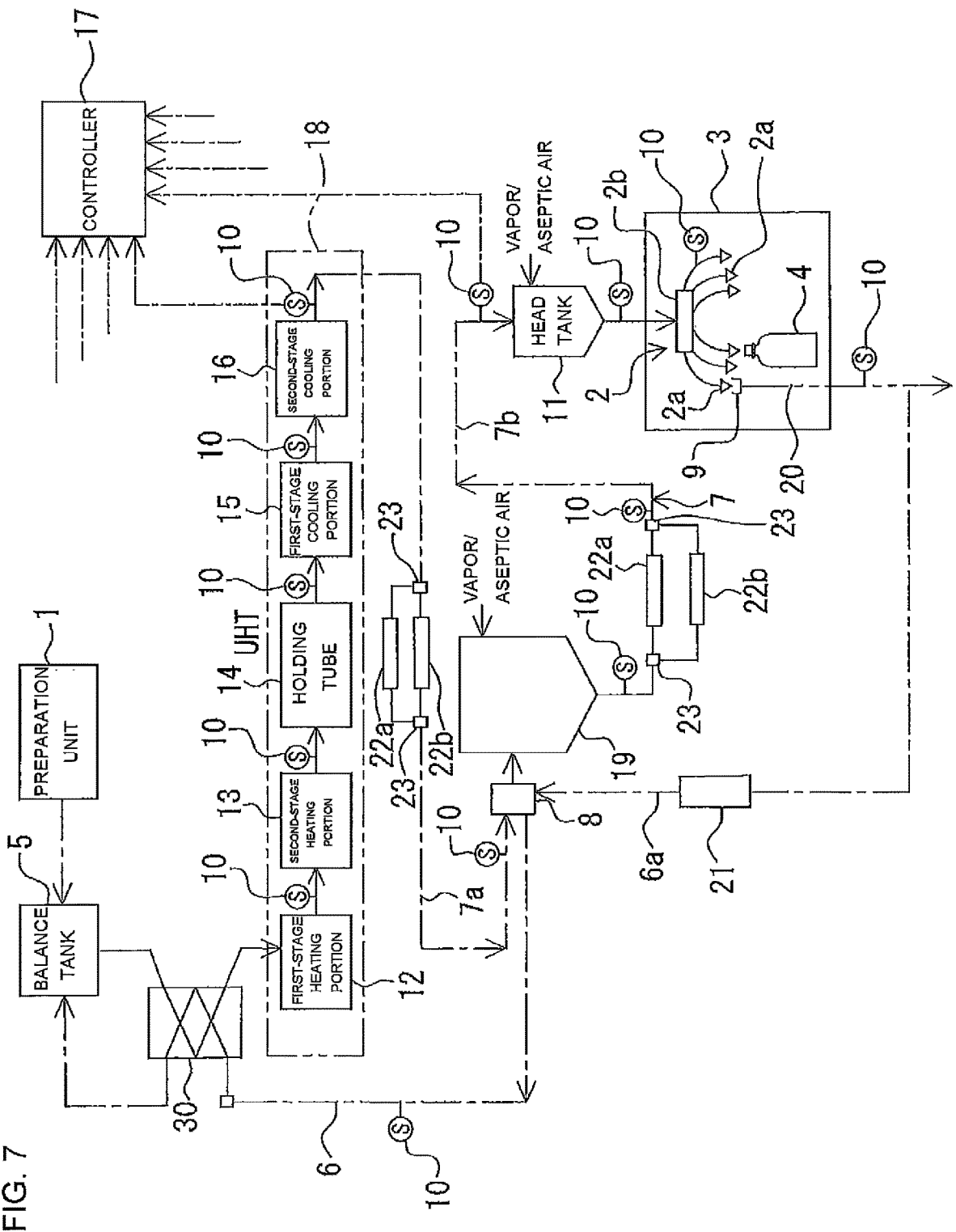
FIG. 7 is a block diagram showing a modification of the drink filling apparatus to which the cleaning and sterilization method according to the present invention is applied.
Figure 8:
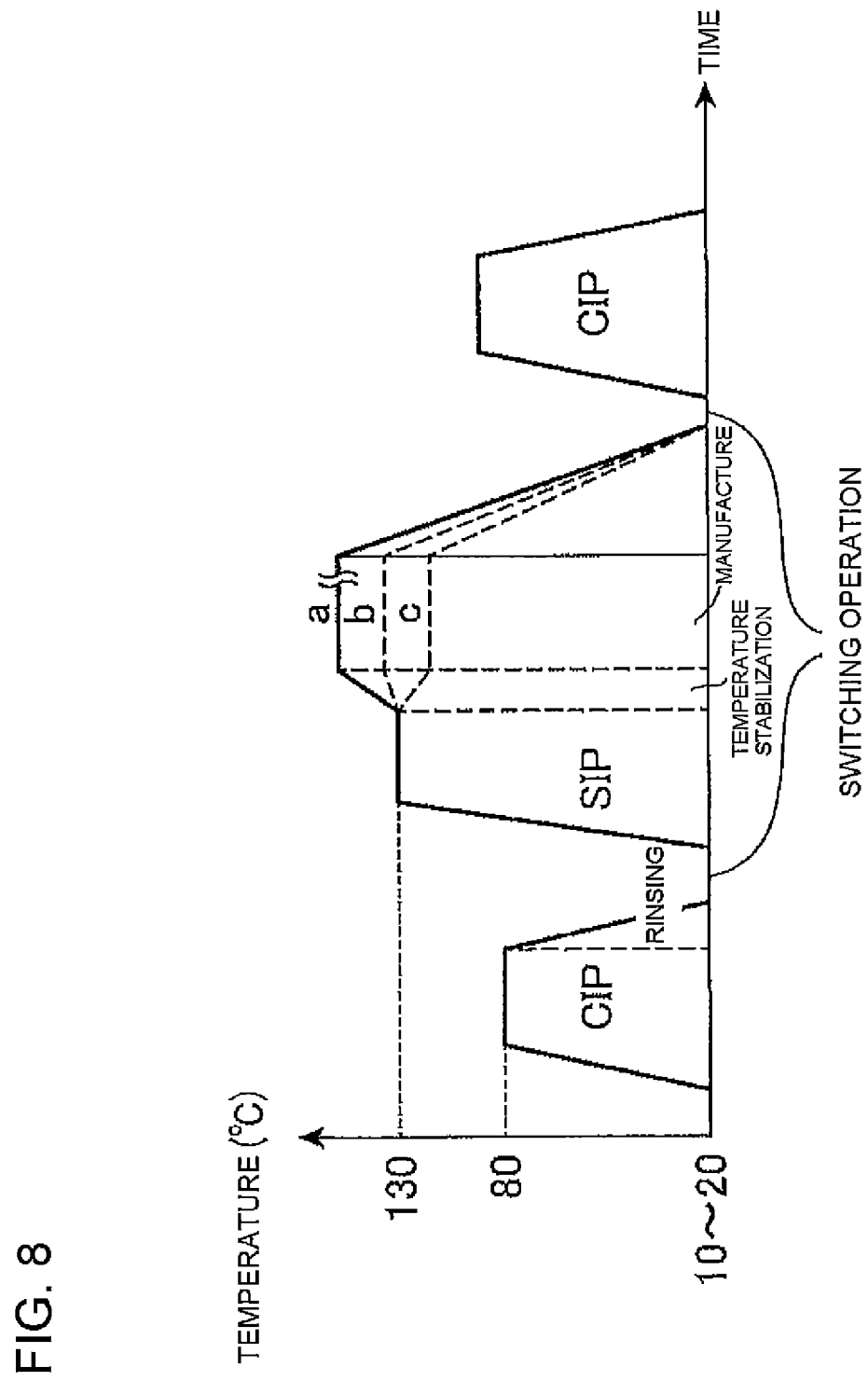
FIG. 8 is a graph for illustrating a variation in temperature in the CIP process, the SIP process and the manufacturing step in a conventional cleaning and sterilization method.

Although the present invention is configured as described above, the present invention is not limited to the embodiments described above, and various modifications can be made within the scope of the spirit of the present invention. The manifold valve 8 may be omitted, and the CIP and SIP processes for the components from the sterilizer to the filler can be performed at the same time, and control of the temperature stabilization step described above can also be performed. Although the aseptic surge tank 19 and the head tank 11 in the downstream-side piping section 7b are subjected to the CIP process and the SIP process at the same time as described above, the aseptic surge tank 19 and the head tank 11 can be separately subjected to the CIP process and the SIP process. In that case, the amount of the liquid residing in the piping is reduced, and the CIP process and the SIP process can be completed in a shorter time. Although, in this specification, a shell and tube type heat exchanger has been described as an example of the UHT (heating sterilization part) according to the present invention, the UHT is not limited to this type, and a plate type heat exchanger can also be used, for example. Furthermore, not only these indirect heating schemes but also direct heating schemes can be used. Furthermore, the present invention has been described with regard to the drink filling apparatus used for filling with a drink as a product, the product is not limited to drinks, and the drink filling apparatus can be applied to filling with a medicine, a food, a liquid food or a drink containing a solid material. Furthermore, although the transition from the CIP process to the SIP process has been described with regard to a case where the temperature for the SIP process is the same as the set temperature for the CIP process, the CIP process may be performed at a lower temperature than the SIP process, or the CIP process may be performed at a higher temperature than the SIP process. Furthermore, as shown in FIG. 7, a heat exchanger 30 may be arranged between the UHT 18 and the balance tank 5 (or at a position preceding the balance tank 5) as required. The heat exchanger 30 can exchange heat between the cleaner for cleaning or sterilizing the interior of the drink supply piping raised in temperature in the UHT 18 or the water for rinsing the interior of the drink supply piping 7 raised in temperature in the UHT 18 and the cleaner at a lower temperature (80° C., for example) supplied from the balance tank 5 or water, thereby raising the temperature of the cleaner supplied from the balance tank 5 to the UHT 18. In this way, the heat exchanger 30 can reduce the burden on the UHT 18 when raising the temperature of the cleaner or water and improve the thermal efficiency.

The time interval at which the F value is measured and integrated is not limited to 1 minute but can be 1 to 5 seconds. The time interval can be changed depending on the capability of the measuring instrument or the like.

REFERENCE NUMERALS 2 filling machine
6 upstream-side feedback path
7 drink supply piping
7a upstream-side piping section
7b downstream-side piping section
18 heating sterilization part

The invention claimed is:

1. A method of cleaning and sterilizing a drink filling apparatus that includes drink supply piping that feeds a product into a filling machine through a heating sterilization part, the method comprising a CIP process of circulating a cleaner in the drink supply piping to remove a remaining foreign matter from a product on an interior of the drink supply piping and an SIP process of sterilizing the interior of the drink supply piping,
- wherein the CIP process and the SIP process are performed at the same time or in sequence without an interruption between the CIP process and the SIP process,
- the SIP process uses the cleaner circulating in the drink supply piping to sterilize the interior of the drink supply piping,
- after the SIP process, while the cleaner is kept circulating, a temperature condition at a predetermined position in the heating sterilization part is adjusted to a predetermined temperature for manufacture of filling with a drink, and
- after the temperature condition at the predetermined position in the heating sterilization part is adjusted to the predetermined temperature for the manufacture, the cleaner in the drink supply piping is removed.

2. The method of cleaning and sterilizing a drink filling apparatus according to claim 1, wherein the cleaner in the drink supply piping is removed by flowing aseptic water in the drink supply piping.

* * * * *